(12) United States Patent
Uekita et al.

(10) Patent No.: US 9,199,952 B2
(45) Date of Patent: Dec. 1, 2015

(54) METHOD FOR PRODUCING COMPOSITION CONTAINING FUCOXANTHIN

(71) Applicant: KANEKA CORPORATION, Osaka-shi (JP)

(72) Inventors: Ken Uekita, Takasago (JP); Tadashi Moroshima, Takasago (JP)

(73) Assignee: KANEKA CORPORATION, Osaka-shi (JP)

(*) Notice: Subject to any disclaimer, the term of this patent is extended or adjusted under 35 U.S.C. 154(b) by 0 days.

(21) Appl. No.: 14/391,880

(22) PCT Filed: Feb. 27, 2013

(86) PCT No.: PCT/JP2013/055131
§ 371 (c)(1),
(2) Date: Oct. 10, 2014

(87) PCT Pub. No.: WO2013/161378
PCT Pub. Date: Oct. 31, 2013

(65) Prior Publication Data
US 2015/0065568 A1    Mar. 5, 2015

(30) Foreign Application Priority Data

Apr. 27, 2012  (JP) ................. 2012-103689

(51) Int. Cl.
| | | |
|---|---|---|
| *A61K 31/335* | (2006.01) | |
| *C07D 303/00* | (2006.01) | |
| *C07D 301/32* | (2006.01) | |
| *A23L 1/30* | (2006.01) | |
| *A61K 31/336* | (2006.01) | |
| *C07D 303/32* | (2006.01) | |

(52) U.S. Cl.
CPC ............. *C07D 301/32* (2013.01); *A23L 1/30* (2013.01); *A61K 31/336* (2013.01); *C07D 303/32* (2013.01)

(58) Field of Classification Search
CPC .. C07D 303/14; C07D 303/16; C07D 303/17; C07D 303/32; C07D 301/32; A61K 31/336; A23L 1/30

USPC ............................... 549/546; 514/475
See application file for complete search history.

(56) References Cited

U.S. PATENT DOCUMENTS

2003/0054070 A1    3/2003   Bridges et al.

FOREIGN PATENT DOCUMENTS

| JP | 2004 75634 | 3/2004 |
|---|---|---|
| JP | 2008 255231 | 10/2008 |
| JP | 2009 120494 | 6/2009 |
| JP | 2010 120939 | 6/2010 |
| JP | 2010 235574 | 10/2010 |
| JP | 2011 256153 | 12/2011 |
| JP | 2011256153 | * 12/2011 |

OTHER PUBLICATIONS

Wayne W. Fish. "Novel Procedure for the Extraction and Concentration of Carotenoid-Containing Chromoplasts from Selected Plant Systems", Journal of Agricultural and Food Chemistry, vol. 55, No. 4, pp. 1486-1490.

International Search Report Issued Apr. 2, 2013 in PCT/JP13/055131 Filed Feb. 27, 2013.

* cited by examiner

*Primary Examiner* — T. Victor Oh
(74) *Attorney, Agent, or Firm* — Oblon, McClelland, Maier & Neustadt, L.L.P.

(57) ABSTRACT

A method for producing a composition containing fucoxanthin includes a first step of adding a water-soluble solvent containing 0 to 80% by weight of water to seaweed to obtain a seaweed component extract, and then adding water and/or a water-soluble solvent to the seaweed component extract in such a manner that the concentration of the water-soluble solvent is 20 to 45% by weight and also adding a diluent thereto to obtain a diluent-containing extract, and a second step of stirring the diluent-containing extract, and then collecting a substance aggregating into the diluent-containing extract as a composition containing fucoxanthin by separation.

20 Claims, No Drawings

METHOD FOR PRODUCING COMPOSITION CONTAINING FUCOXANTHIN

TECHNICAL FIELD

The present invention relates to a method for producing a composition containing fucoxanthin.

BACKGROUND ART

Carotenoids are yellow to red pigments naturally present in plants, animals, seaweed, microorganisms, and the like and antioxidant action is known as the typical action thereof. In particular, xanthophylls containing an oxygen atom in the molecular structure, such as astaxanthin, fucoxanthin, lutein, canthaxanthin, and zeaxanthin, have high antioxidant action. In particular, fucoxanthin has been reported to have functionalities, such as antiobesity action, anticancer action, antidiabetic action, and antiinflammatory action, and has potential of exhibiting a high utility value as a functional material.

In general, even in the case of cells that produce carotenoid, the content of the carotenoid contained in the cells is low. For example, fucoxanthin contained in seaweed is extremely as small as about 0.01%. In order to take fucoxanthin in an amount which allows the fucoxanthin to exert effective functionalities, it is necessary to eat a huge amount of seaweed, which is not realistic. Therefore, in order to prepare fucoxanthin into a practical functional material, it is necessary to extract and purify fucoxanthin from seaweed with a large amount of solvent, and then highly purifying the same to about several % concentration by concentration.

As a method for highly purifying fucoxanthin, the following method is known. JP-A No. 2004-75634 (Patent Document 1) describes a method for removing impurities by treating an extract obtained from seaweed with activated carbon. However, according to the method, only partial impurities such as chlorophyll, adsorbing to the activated carbon, can be removed, so that the purification degree of the fucoxanthin is low. Furthermore, the fucoxanthin itself tends to be adsorbed to the activated carbon to be removed, and thus fucoxanthin cannot be prepared into a practical functional material only by this operation. JP-A No. 2009-120494 (Patent Document 2) describes a method including bringing an extract from brown algae into contact with a synthetic adsorption resin, and then eluting fucoxanthin adsorbing to the resin. However, according to the method, fucoxanthin can be highly purified up to about several % but a large amount of an expensive synthetic adsorption resin is used for obtainable fucoxanthin, which increases the cost, resulting in the fact that the method is economically disadvantageous. Moreover, in order to elute the fucoxanthin adsorbed to the surface of the synthetic adsorption resin, a large amount of solvent is required and also an operation of concentrating and distilling off the used solvent is required. However, since the fucoxanthin is very unstable to heat, an operation of concentrating and distilling off a large amount of solvent is required. Therefore, it can be said that the method for highly purifying fucoxanthin using the synthetic adsorption resin has poor production efficiency and also is industrially disadvantageous.

The production method including highly purifying fucoxanthin is disclosed as described above, but a method for highly purifying fucoxanthin without using the operation of concentrating a large amount of solvent has not been disclosed yet, so that problems with cost and operability in producing fucoxanthin have not been solved yet.

CITATION LIST

Patent Literatures

Patent Document 1: JP-A No. 2004-75634
Patent Document 2: JP-A No. 2009-120494

SUMMARY OF INVENTION

Technical Problem

It is an object of the present invention to solve the above-described problems in highly purifying fucoxanthin extracted from seaweed. Specifically, the present invention provides a production method including obtaining a high concentration of carotenoid without using a heat treatment process. Furthermore, the present invention provides a production method which can increase the concentration of fucoxanthin without using a synthetic adsorption resin when highly purifying the same and is excellent in terms of cost and operability.

Solution to Problem

The present inventors have repeatedly conducted extensive research in order to solve the above-described problems. As a result, surprisingly, the present inventors have found that after an extract of a seaweed component of seaweed is obtained, water and/or a water-soluble solvent are/is added in such a manner that the concentration of the water-soluble solvent is fixed and also a diluent is added to thereby obtain a diluent-containing extract, and then the diluent-containing extract is stirred, whereby fucoxanthin can be efficiently highly purified and an aggregate containing a plenty of useful lipid components of seaweed can be obtained. Furthermore, the present inventors have found that the arsenic content of a composition containing fucoxanthin obtained by the present invention remarkably decreases as compared with the arsenic content contained in seaweed as the raw material, and thus the present invention has been accomplished.

More specifically, those provided by the present invention are as follows.

(1)

A method for producing a composition containing fucoxanthin includes a first step of adding a water-soluble solvent containing 0 to 80% by weight of water to seaweed to obtain a seaweed component extract, and then adding water and/or a water-soluble solvent into the seaweed component extract in such a manner that the concentration of the water-soluble solvent is 20 to 45% by weight and also adding a diluent thereinto to obtain a diluent-containing extract, and a second step of stirring the diluent-containing extract, and then collecting a substance aggregating in the diluent-containing extract as a composition containing fucoxanthin by separation.

(2)

The method for producing a composition containing fucoxanthin according to (1), in which the diluent is added to the seaweed component extract in such a manner as to exceed the solubility in the first step.

(3)

The method for producing a composition containing fucoxanthin according to (1) or (2), in which the diluent has solubility of 0 to 10 g in 100 g of water.

(4)

The method for producing a composition containing fucoxanthin according to any one of (1) to (3), in which the diluent is added in a proportion of 0.001 to 100% by weight based on the seaweed component extract in the first step.

(5)

The method for producing a composition containing fucoxanthin according to any one of (1) to (4), in which the composition containing fucoxanthin contains lipid other than the fucoxanthin in a proportion of 0.05 to 100 times the weight of fucoxanthin and the mass of arsenic in the composition containing fucoxanthin is 5% or less of the mass of arsenic contained in the seaweed serving as the raw material.

(6)

The method for producing a composition containing fucoxanthin according to (5), in which the content of eicosapentaenoic acid is 10% by weight or more among lipids in the composition containing fucoxanthin.

(7)

A method for producing a concentrate containing fucoxanthin, includes adding a solvent to the composition containing fucoxanthin obtained by the method according to any one of (1) to (6) to elute lipid containing the fucoxanthin, and then concentrating and distilling off the solvent in the eluate.

(8)

A method for producing an oil containing fucoxanthin, includes adding at least oil to the concentrate containing fucoxanthin obtained by the method according to (7).

Advantageous Effects of Invention

The method according to the present invention does not require an expensive synthetic adsorption resin and a complicated purifying operation, and thus can efficiently and economically increase the concentration of fucoxanthin. Furthermore, according to the method, lipid components, such as fatty acid, in seaweed can be simultaneously obtained as an aggregate in addition to fucoxanthin and also a composition containing fucoxanthin in which the mass of arsenic in the aggregate is 5% or less of the mass of arsenic contained in the seaweed serving as the raw material can be obtained.

DESCRIPTION OF EMBODIMENTS

The present invention is described in detail below.

In the present invention, after a water-soluble solvent is added to seaweed to obtain a seaweed component extract, water and/or a water-soluble solvent are/is added in such a manner that the concentration of the water-soluble solvent is fixed and also a diluent is added thereto to obtain a diluent-containing extract, and then the diluent-containing extract is stirred to aggregate a lipid component containing fucoxanthin to obtain a composition containing fucoxanthin.

The seaweed for use in the present invention is not particularly limited insofar as fucoxanthin is contained but seaweed belonging to the phaeophyceae containing a relatively large amount of fucoxanthin is preferable. In particular, in view of the resource amount and the market distribution properties, Sargassum such as *Sargassum fulvellum* and *Sargassum horneri*, Hijiki, Wakame, Kombu, Mozuku, and the like are more preferable. These kinds of seaweed may be nature seaweed or cultured seaweed and may be used alone or as a mixture of two or more kinds thereof. Moreover, the seaweed can be used in any state, such as seaweed as it is collected from the sea, frozen seaweed, salt-cured seaweed, dried seaweed, and seaweed subjected to treatment such as water-washing treatment, hot water treatment, acid water washing, alkaline water washing, chipping, and the like. The chipping refers to processing treatment of chipping seaweed to a size of about 50 mm, for example, from the viewpoint of an improvement of extraction efficiency, ease of handling, and the like.

A method for obtaining a seaweed component extract from the seaweed mentioned above is not particularly limited insofar as a lipid component containing fucoxanthin can be extracted and the seaweed component extract can be obtained in accordance with a usual method. The solvent for use in this process is a water-soluble solvent and the solvent is not particularly limited insofar as the solvent is a water-soluble solvent in which fucoxanthin can dissolve. Examples of the solvents include alcohol solvents such as methanol, ethanol, n-propanol, isopropanol, n-butanol, tert-butanol, and ethylene glycol; ether solvents such as tetrahydrofuran; ketone solvents such as acetone and methyl ethyl ketone; nitrile solvents such as acetonitrile and propionitrile; sulfoxide solvents such as dimethylsulfoxide; amide solvents such as N,N-dimethyl formamide, N,N-dimethyl acetamide, and N,N-diethyl acetamide; and the like. The water-soluble solvents may be used alone or as a mixture of two or more kinds thereof. When mixing two or more kinds thereof, the mixing ratio is not particularly limited. However, it is particularly preferable to select ethanol among the water-soluble solvents mentioned above from the viewpoint of safely applying the obtained one to foods, pharmaceuticals, cosmetics, and the like as a functional material.

In the present invention, the content of the water in the water-soluble solvent to be added to seaweed is preferably 0 to 80% by weight, more preferably 0 to 60% by weight, and still more preferably 0 to 40% by weight.

As the temperature when extracting a seaweed component from seaweed, the extraction can be performed at generally −20 to 100° C., usually −10 to 60° C., and preferably 0 to 40° C. As the extraction time, the extraction can be performed for usually 0.1 hours to 7 days and preferably 0.5 hours to 2 days. The use amount of the water-soluble solvent is preferably an amount 0.1 times or more and 50 times or less and more preferably 1 times or more and 20 times or less the amount of the seaweed. When the amount is less than 1 times the amount of the seaweed, the seaweed is not sufficiently immersed in the solvent, so that the recovery rate of the seaweed component becomes low. When the amount is 50 times or more the amount of the seaweed, the solvent cost increases and the productivity decreases, and thus the amount is economically disadvantageous.

Thereafter, the seaweed component extract is separated from the solid content to be collected by a usual method using centrifugal separation, pressure filtration, a filter pressing machine, decantation, or the like.

Examples of the seaweed component dissolved in the seaweed component extract thus obtained include, depending on the type of the seaweed to be used, fucoxanthin, fatty acids such as phospholipid, glycolipid, neutral fat, eicosapentaenoic acid, hexadecatetraenoic acid, and octadecatetraenoic acid, polysaccharides such as alginic acid and fucoidan, arsenic compounds such as arseno sugar and arsenic acid, iodine, and the like.

Next, the first step of adding water and/or a water-soluble solvent into the seaweed component extract in such a manner that the water-soluble solvent concentration is 20 to 45% by weight and also adding a diluent thereto to obtain a diluent-containing extract is described.

The water-soluble solvent to be added in the first step can be selected as appropriate from the same water-soluble solvents as those which can be added to seaweed when obtaining the seaweed component extract for use.

In the present invention, water and/or a water-soluble solvent are/is added to the seaweed component extract to obtain a diluent-containing extract. Herein, the weight of the water-soluble solvent based on the diluent-containing extract is preferably 20 to 45% by weight in total of the water-soluble solvent added when obtaining the seaweed component extract and the water-soluble solvent added in the first step. Herein, the composition of 20 to 45% by weight refers to a ratio obtained in the case where the calculation is performed without adding the weight of the diluent added together to the total solution weight. The composition is a composition suitable for aggregation of the lipid component containing fucoxanthin and allows fucoxanthin to be efficiently aggregated to the diluent serving as a core substance described later to be collected as an aggregate by the following separation. Herein, when the water-soluble solvent is less than 20% by weight, the lipid component containing fucoxanthin is deposited but aggregation does not occur. Therefore, fucoxanthin cannot be collected as an aggregate with the diluent by the following separation and is discharged into a filtrate. On the other hand, when the water-soluble solvent exceeds 45% by weight, the lipid component containing fucoxanthin is still dissolving and is not deposited, and thus cannot be collected as an aggregate by separation.

As the diluent to be added to the seaweed component extract together with the water and/or the water-soluble solvent described above in the first step of the present invention, a compound which adsorbs fucoxanthin by chemical bond of a synthetic adsorption resin or the like is not suitable and one which physically functions as a core substance of promoting aggregation of the lipid component containing fucoxanthin which is deposited in a diluent-containing extract composition described later may be acceptable. Specifically, a diluent having solubility of preferably 0 to 10 g in 100 g of water, more preferably 0 to 7 g in 100 g of water, and still more preferably 0 to 5 g in 100 g of water. As a diluent whose solubility in water is higher than the solubility of 10 g in 100 g of water, the amount required for the diluent to function as a nuclear substance increases, which is economically disadvantageous.

Since the diluent in the present invention has a necessity of functioning as a core substance of aggregation, it is preferable to use the diluent in an amount equal to or higher than the amount which achieves solubility. The solubility in the present invention is generally a limit in which a substance dissolves in a solvent. Therefore, "equal to or higher than the solubility" refers to a state where a solute is present in a solvent without dissolution. Among the diluents, edible powder such as flour, soybean flour, microcrystalline cellulose, and cyclodextrin can be used from the viewpoint that fucoxanthin is used as food additives, and it is possible to eat the same as powder to which fucoxanthin adheres. Moreover, when the filterability of liquid after aggregation is poor, which makes it difficult to perform solid-solution separation, diatomite, kaolin, silica dioxide, and the like which are common filter aids can be suitably used as the diluent.

As the addition amount of the diluent in the first step, it is preferable to add the diluent in a proportion of 0.001 to 100% by weight based on the seaweed component extract. The proportion is more preferably 0.005 to 50% by weight and still more preferably 0.01 to 10% by weight. When the addition amount of the diluent is smaller than 0.001% by weight based on the seaweed component extract, there are problems that since a sufficient aggregation promotion effect caused by the addition of the diluent cannot be obtained, it takes a long time to obtain an aggregate and since the function as a filter aid cannot be sufficiently performed, the filterability remarkably deteriorates, for example. When the addition amount of the diluent is larger than 100% by weight based on the seaweed component extract, there are problems that the fluidity deteriorates to hinder the stirring and the concentration of the fucoxanthin in the aggregate is low, resulting in the fact that the obtained one is not practically used, for example. Therefore, the addition amount is not preferable.

Next, the second step of stirring the diluent-containing extract, and then collecting a substance aggregating in the diluent-containing extract by separation is described.

In the present invention, as a method for stirring the diluent-containing extract is not particularly limited insofar as the solution can be uniformly mixed, and usual methods such as a method using a stirring blade and a method using a line mixer are mentioned. The aggregation is promoted by the stirring operation and also uniform aggregation to the diluent serving as a core substance can be achieved. Moreover, as the stirring conditions, from the viewpoint of suppressing the decomposition of the fucoxanthin, generally, the temperature is preferably 60° C. or less and more preferably 40° C. or less. As the aggregation time, the aggregation can be performed for usually 0.1 hours to 2 days and preferably 0.5 hours to 6 hours.

After the stirring, the substance aggregating to the core substance is a lipid component contained in the seaweed. It is a matter of course that fucoxanthin is mentioned and, for example, fatty acids such as phospholipid, glycolipid, neutral fat, eicosapentaenoic acid, hexadecatetraenoic acid, and octadecatetraenoic acid, and the like are also mentioned.

In the present invention, a composition containing fucoxanthin can be collected by separating the aggregated substance from the diluent-containing extract. As a method for separating the same is not particularly limited insofar as the aggregate can be separated from the liquid in the system. For example, the aggregate can be collected by usual methods using centrifugal separation, pressure filtration, filtration under reduced pressure, membrane filtration, a filter pressing machine, decantation, and the like.

The composition containing fucoxanthin in the present invention is preferable in that plenty of lipid having functionality such as eicosapentaenoic acid and hexadecatetraenoic acid contained in seaweed is contained and the lipid other than the fucoxanthin is contained in a proportion of 0.05 to 100 times the weight of fucoxanthin. When the weight of the lipid other than fucoxanthin is smaller than 0.05 times the weight of the fucoxanthin, there is a problem that most lipid components are contained in a filtrate, so that the recovery rate as the absolute amount of the lipid including fucoxanthin is low. When the weight of the lipid other than fucoxanthin is larger than 100 times the weight of the fucoxanthin, the weight is not preferable from the viewpoint that the fucoxanthin content in the composition relatively decreases, and therefore the fucoxanthin cannot be highly purified. In the composition containing fucoxanthin, the content of the eicosapentaenoic acid is usually 10% or more among the lipids usually contained in the composition.

The mass of arsenic in the composition containing fucoxanthin is preferably 5% or less, more preferably 4% or less, and still more preferably 3% or less of the mass of arsenic contained in the seaweed serving as the raw material. When the mass of arsenic in the composition based on the mass of arsenic contained in the seaweed serving as the raw material is larger than 5%, it is imagined that the composition adversely affects a human body when developed to foods.

In the present invention, the composition containing fucoxanthin obtained by separation may be collected as it is or a concentrate containing fucoxanthin may be obtained by eluting the lipid component containing the fucoxanthin with a small amount of solvent once, and then concentrating and distilling off the eluate. Furthermore, an oil containing fucoxanthin can be produced by adding at least oil to the concentrate containing fucoxanthin.

The concentrate containing fucoxanthin refers to a composition in which the fucoxanthin content is higher than that of the composition containing fucoxanthin obtained by separation and the fucoxanthin contained in the composition is purified and the fucoxanthin content is, not particularly limited thereto, preferably 0.001 to 50% by weight and more preferably 0.01 to 50% by weight.

As the small amount of solvent used in order to elute the lipid component containing fucoxanthin from the composition containing fucoxanthin is not particularly limited insofar as the fucoxanthin can be eluted, and can be selected as appropriate from the same water-soluble solvents as those which can be added to seaweed when obtaining the seaweed component extract for use.

The operation method for concentrating and distilling off the eluate is not particularly limited insofar as the solvent can be distilled off and distillation under reduced pressure, atmospheric distillation, and the like are mentioned, for example.

As the conditions of concentrating and distilling off the eluate, the eluate is concentrated and distilled off at preferably 80° C. or lower and more preferably 70° C. or lower from the viewpoint of suppressing decomposition of the fucoxanthin.

When producing the oil containing fucoxanthin in the present invention, at least oil needs to be added. The oil for use in this process is not particularly limited insofar as the oil can be eaten as a food. Examples of the oil include coconut oil, palm oil, palm kernel oil, flaxseed oil, tsubaki oil, brown rice germ oil, rapeseed oil, rice bran oil, olive oil, peanut oil, corn oil, wheat germ oil, soybean oil, perilla oil, cottonseed oil, sunflower seed oil, kapok oil, evening primrose oil, sesame oil, safflower oil, medium chain fatty acid triglyceride, fish oil, and the like. In order to improve the mixed state of the oil and the fucoxanthin, an emulsifier and the like may be added. Such an emulsifier is not particularly limited and examples of the emulsifier include glycerin fatty acid ester, sorbitan fatty acid ester, propylene glycol fatty acid ester, sucrose fatty acid ester, polyglycerol fatty acid ester, polyglycerol condensed ricinoleic acid ester, lecithin, enzyme treated lecithin, and the like. Furthermore, in order to increase the stability of the oil containing fucoxanthin, an antioxidization agent may be added. Such an antioxidization agent is not particularly limited and examples of the antioxidization agent include vitamin E, vitamin C, vitamin C derivatives, and the like. As described above, the oil containing fucoxanthin may contain at least oil, and other additives may be set as appropriate.

As described above, by the use of the method for producing the composition containing fucoxanthin including the first step of adding a water-soluble solvent containing 0 to 80% by weight of water to seaweed to obtain a seaweed component extract, and then adding water and/or a water-soluble solvent into the seaweed component extract in such a manner that the concentration of the water-soluble solvent is 20 to 45% by weight, and also adding a diluent thereinto to obtain a diluent-containing extract, and the second step of stirring the diluent-containing extract, and then collecting a substance aggregating into the diluent-containing extract by separation, the composition containing fucoxanthin can be efficiently and economically obtained without using the synthetic adsorption resin and also without concentrating a large amount of an extraction solvent. The composition containing fucoxanthin can be used as functional materials such as foods, pharmaceuticals, and cosmetics by using the same as it is or preparing the same into the oil containing fucoxanthin as described above as required and can be provided in the following aspects.

Examples of the aspects provided as foods include, not limited thereto, beverages (soft drinks, drinks, and the like), hard and soft capsules, tablets, candies, chewing gums, Gummi, cookies, chocolates, wafers, jellies, and the like.

When utilized as pharmaceuticals, the fucoxanthin containing substance is given as it is or in various kinds of dosage forms formed by adding a diluent, a binding agent, a disintegrator, and suitable other additives and the like thereto, such as an aerosol, a liquid, an extract, an elixir, a capsule, a granule, a pill, an ophthalmic ointment, a percutaneous absorption preparation, a suspension, an emulsion, a suppository, a powder, a spirit, a tablet, a syrup, an injection, a pasting agent, a tincture, eye drops, a troche agent, an ointment, a cataplasm, an aromatic water, a liniment, a lemonade, a fluid extract, and a lotion according to each patient, the pathology, and the like but the aspects are not limited thereto.

As aspects given as cosmetics and the like, a lotion, a pack, a body gell, a hand cream, a lip cream, a shampoo agent, and the like are mentioned but the aspects are not limited thereto.

In order to use the same for the use mentioned above, the composition containing fucoxanthin may be combined with compounds which are permitted in foods, pharmaceuticals, and cosmetics. Examples of the compounds include essential oil, fat, lanolin, vaseline, paraffin, wax, glycols, alcohols, water, an emulsifier, a suspending agent, citric acid, hydrochloric acid, tartaric acid, lactic acid, vitamins, gelatin, and the like and the compounds may be used alone or in combination of two or more kinds thereof and the mixing ratio is not particularly limited.

The fucoxanthin can be quantitatively measured by HPLC or the like. The arsenic can be quantitatively measured by atomic absorptiometry or the like. The lipid amount and the fatty acid composition in the lipid can be quantitatively measured by GC-MS or the like.

EXAMPLES

Hereinafter, the present invention is more specifically described with reference to Examples but the present invention is not limited to the Examples.

Example 1

Example of Aggregation Using Soybean Flour 1500 g of a 60% ethanol aqueous solution was added to 300 g of *Sargassum horneri* which was frozen and then chipped to 10 mm or less, stirred at 25° C. for 1 hour, filtered, and then washed with 300 g of the 60% ethanol aqueous solution to obtain 1970 g of a seaweed component extract. Thereafter, 1400 g of water was added to the seaweed component extract in such a manner that the ethanol concentration was 33% and also 500 mg of soybean flour was added thereto. Thereafter, the resultant mixture was stirred at 25° C. for 1 hour to generate an aggregate in the system. The resultant substance was filtered to collect 1289 mg of an aggregate. The fucoxanthin concentration of the aggregate was 2.56% as measured by HPLC in accordance with a usual method. The mass of arsenic in the aggregate was 2.3% as measured by atomic absorptiometry in accordance with a usual method.

Comparative Example 1

Comparative Control Without Diluent 1500 g of a 60% ethanol aqueous solution was added to 300 g of *Sargassum horneri* which was frozen and then chipped to 10 mm or less, stirred at 25° C. for 1 hour, filtered, and then washed with 300 g of the 60% ethanol aqueous solution to obtain 1970 g of a seaweed component extract. Thereafter, 1400 g of water was added to the seaweed component extract to adjust the ethanol concentration to 33%, and then the resultant mixture was stirred at 25° C. for 1 hour. The resultant substance was filtered but an aggregate was not able to obtain.

Example 2

Example of Increasing Concentration by Re-Aggregation

An aggregate obtained in the same manner as in Example 1 was added to 300 g of a 60% ethanol aqueous solution, 214 g of water was added to adjust the ethanol concentration based on the total concentration to 35%, and then the resultant mixture was stirred at 25° C. for 2 hours to generate an aggregate in the system. The resultant substance was filtered to collect 830 mg of an aggregate. The fucoxanthin concentration of the aggregate was 4.00% as measured by HPLC in accordance with a usual method. The mass of arsenic in the aggregate was 0.4% as measured by atomic absorptiometry in accordance with a usual method.

Example 3

Example Using Ethanol Solvent for Extraction 300 g of ethanol was added to 200 g of *Sargassum horneri*, stirred at 25° C. for 2 hours, and then filtered to obtain 380 g of a seaweed component extract. Thereafter, 266 g of water was added to the seaweed component extract in such a manner that the ethanol concentration was 40% and also 2.0 g of diatomite was added. Thereafter, the resultant mixture was stirred at 25° C. for 1 hour to generate an aggregate in the system. The resultant substance was filtered to obtain 2.23 g of an aggregate. 4.0 g of ethanol was poured to the aggregate to elute a lipid component, and then the solvent of the eluate was concentrated and distilled off, whereby 212 mg of a concentrate was obtained. The fucoxanthin concentration of the aggregate was 6.52% as measured by HPLC in accordance with a usual method. Furthermore, cooking oil, lecithin, and vitamin E were added to the concentrate, and then uniformly mixed, whereby 1.26 g of an oil containing 1.0% of fucoxanthin was obtained.

Example 4

Example Using 80% Ethanol Aqueous Solution for Extraction 300 g of an 80% ethanol aqueous solution was added to 200 g of *Sargassum horneri*, stirred at 25° C. for 2 hours, and then filtered to obtain 370 g of a seaweed component extract. Thereafter, 201 g of water was added to the seaweed component extract in such a manner that the ethanol concentration was 35% and also 10.0 g of diatomite was added thereto. Thereafter, the resultant mixture was stirred at 25° C. for 1 hour to generate an aggregate in the system. The resultant substance was filtered to obtain 10.18 g of an aggregate. 10.0 g of ethanol was poured to the aggregate to elute a lipid component, and then the solvent of the eluate was concentrated and distilled off, whereby 122 mg of a concentrate was obtained. The fucoxanthin concentration of the aggregate was 9.83% as measured by HPLC in accordance with a usual method. Furthermore, cooking oil, glycerin fatty acid ester, and vitamin E were added to the concentrate, and then uniformly mixed, whereby 1.17 g of an oil containing 1.0% of fucoxanthin was obtained.

Example 5

Example of Adjusting Ethanol Concentration to 45%

150 g of a 60% ethanol aqueous solution was added to 30 g of *Sargassum horneri*, stirred at 25° C. for 1 hour, filtered, and then washed with 30 g of the 60% ethanol aqueous solution to obtain 200 g of a seaweed component extract. Then, 31 g of water was added to the seaweed component extract in such a manner that the ethanol concentration was 45% and also 75 mg of diatomite was added. Thereafter, the resultant mixture was stirred at 25° C. for 1 hour to generate an aggregate in the system. The resultant substance was filtered to obtain 100.1 mg of an aggregate. The fucoxanthin concentration of the aggregate was 0.50% as measured by HPLC in accordance with a usual method.

Example 6

Example of Adjusting Ethanol Concentration to 30%

The same operations as those in Example 5 were performed, except that the amount of water added to the seaweed component extract was 145 g and the ethanol concentration was adjusted to 30%, whereby 96.1 mg of an aggregate was obtained. The fucoxanthin concentration of the aggregate was 2.24% as measured by HPLC in accordance with a usual method.

Example 7

Example of Adjusting Ethanol Concentration to 20%

The same operations as those in Example 5 were performed, except that the amount of water added to the seaweed component extract was 317 g and the ethanol concentration was adjusted to 20%, whereby 87.8 mg of an aggregate was obtained. The fucoxanthin concentration of the aggregate was 0.19% as measured by HPLC in accordance with a usual method.

Comparative Example 2

Example of Adjusting Ethanol Concentration to 55%

150 g of a 60% ethanol aqueous solution was added to 30 g of *Sargassum horneri*, stirred at 25° C. for 1 hour, filtered, and then washed with 30 g of the 60% ethanol aqueous solution to obtain 200 g of a seaweed component extract. Then, 13 g of ethanol was added to the seaweed component extract in such a manner that the ethanol concentration was 55% and also 75 mg of diatomite was added. Thereafter, the resultant mixture was stirred at 25° C. for 1 hour. The resultant substance was filtered to obtain 75.1 mg of an aggregate. The fucoxanthin concentration of the aggregate was 0.01% or less as measured by HPLC in accordance with a usual method.

Comparative Example 3

Example of Adjusting Ethanol Concentration to 10%

The same operations as those in Example 5 were performed, except that the amount of water added to the seaweed component extract was 840 g and the ethanol concentration was adjusted to 10%, whereby 76.0 mg of an aggregate was obtained. The fucoxanthin concentration of the aggregate was 0.01% or less as measured by HPLC in accordance with a usual method.

Example 8

Example Using Flour 150 g of a 60% ethanol aqueous solution was added to 30 g of *Sargassum horneri* which was frozen, and then chipped to 10 mm or less, stirred at 15° C. for 15 hours, filtered, and then washed with the 60% ethanol aqueous solution to obtain 196 g of a seaweed component extract. Thereafter, 135 g of water was added to the seaweed component extract in such a manner that the ethanol concentration was 35% and also 3.0 g of flour was added. Thereafter, the resultant mixture was stirred at 15° C. for 3 hours. The resultant substance was filtered to obtain an aggregate, dried by drying under reduced pressure, and then crushed to thereby obtain 2.48 g of dry powder. The fucoxanthin concentration of the dry powder was 0.10% as measured by HPLC in accordance with a usual method.

Example 9

Example Using Microcrystalline Cellulose 150 g of a 60% ethanol aqueous solution was added to 30 g of *Sargassum horneri* which was frozen, and then chipped to 10 mm or less, stirred at 15° C. for 15 hours, filtered, and then washed with the 60% ethanol aqueous solution to obtain 196 g of a seaweed component extract. Thereafter, 135 g of water was added to the seaweed component extract in such a manner that the ethanol concentration was 35% and also 200 mg of microcrystalline cellulose was added. Thereafter, the resultant mixture was stirred at 25° C. for 15 hours. The resultant substance was filtered to obtain an aggregate, dried by drying under reduced pressure, and then crushed to thereby obtain 380 mg of dry powder. The fucoxanthin concentration of the dry powder was 0.53% as measured by HPLC in accordance with a usual method.

Example 10

Example Using Cyclodextrin 150 g of a 60% ethanol aqueous solution was added to 30 g of *Sargassum horneri* which was frozen, and then chipped to 10 mm or less, stirred at 15° C. for 15 hours, filtered, and then washed with the 60% ethanol aqueous solution to obtain 196 g of a seaweed component extract. Then, 135 g of water was added to the seaweed component extract in such a manner that the ethanol concentration was 35% and also 5.0 g of cyclodextrin was added. Then the resultant mixture was stirred at 25° C. for 1 hour. The resultant substance was filtered to obtain an aggregate, dried by drying under reduced pressure, and then crushed to thereby obtain 1.50 g of dry powder. The fucoxanthin concentration of the dry powder was 0.15% as measured by HPLC in accordance with a usual method.

Example 11

Example Using Wakame 50 g of a 60% ethanol aqueous solution was added to 10 g of Wakame, stirred at 25° C. for 18 hours, filtered, and then washed with 10 g of the 60% ethanol aqueous solution to obtain 58 g of a seaweed component extract. Thereafter, 45 g of water was added to the seaweed component extract in such a manner that the ethanol concentration was 35% and also 20 mg of diatomite was added. Thereafter, the resultant mixture was stirred at 25° C. for 2 hours to generate an aggregate in the system. The resultant substance was filtered to obtain 39.6 mg of an aggregate. The fucoxanthin concentration of the aggregate was 1.39% as measured by HPLC in accordance with a usual method.

Example 12

Example Using Kombu 50 g of a 60% ethanol aqueous solution was added to 10 g of Kombu, stirred at 25° C. for 14 hours, filtered, and then washed with 10 g of the 60% ethanol aqueous solution to obtain 60 g of a seaweed component extract. Thereafter, 45 g of water was added to the seaweed component extract in such a manner that the ethanol concentration was 35% and also 20 mg of diatomite was added. Thereafter, the resultant mixture was stirred at 25° C. for 4 hours to generate an aggregate in the system. The resultant substance was filtered to obtain 26.6 mg of an aggregate. The fucoxanthin concentration of the aggregate was 1.76% as measured by HPLC in accordance with a usual method.

Reference Example 1

Fatty Acid Composition Data of Aggregate

As a result of analyzing the fatty acid composition of the aggregate obtained in Example 1 by GC-MS in accordance with a usual method, the eicosapentaenoic acid was 10.5%.

The invention claimed is:
1. A method for producing a composition comprising fucoxanthin, the method comprising:
mixing seaweed with a water-soluble solvent comprising 0 to 80% by weight of water to obtain a seaweed component extract;
mixing the seaweed component extract with water and/or the water-soluble solvent such that a concentration of the water-soluble solvent is 20 to 45% by weight in a mixture;
mixing a diluent with the mixture such that a diluent-containing extract is obtained, and that the diluent forms a core substance which promotes aggregation in the diluent-containing extract; and
collecting, by separation, an aggregate formed by the aggregation in the diluent-containing extract as a composition comprising fucoxanthin.
2. The method according to claim 1, wherein the mixing of the diluent comprises adding the diluent to the mixture in an amount that exceeds solubility of the diluent.
3. The method according to claim 1, wherein the diluent has solubility of 0 to 10 g in 100 g of water.
4. The method according to claim 1, wherein the diluent is mixed in a proportion of 0.001 to 100% by weight based on the seaweed component extract.
5. The method according to claim 1, wherein the composition comprising fucoxanthin comprises lipid other than the fucoxanthin in a proportion of 0.05 to 100 times a weight of fucoxanthin, and a mass of arsenic in the composition comprising fucoxanthin is 5% or less of a mass of arsenic in the seaweed.

6. The method according to claim 5, wherein a content of eicosapentaenoic acid is 10% by weight or more among lipids in the composition comprising fucoxanthin.

7. A method for producing a concentrate comprising fucoxanthin, the method comprising:
   mixing a solvent with the composition comprising fucoxanthin obtained by the method according to claim 1 to obtain an eluate including lipid which comprises the fucoxanthin; and then
   distilling off the solvent in the eluate.

8. A method for producing an oil comprising fucoxanthin, the method comprising:
   mixing at least an oil with a concentrate comprising fucoxanthin obtained by the method according to claim 7.

9. The method according to claim 1, wherein the water and/or the water-soluble solvent are mixed with the seaweed component extract such that the concentration of the water-soluble solvent is 20 to 40% by weight in the mixture.

10. The method according to claim 1, wherein the water and/or the water-soluble solvent are mixed with the seaweed component extract such that the concentration of the water-soluble solvent is 30 to 40% by weight in the mixture.

11. The method according to claim 10, wherein the water-soluble solvent comprises at least one of methanol, ethanol, n-propanol, isopropanol, n-butanol, tert-butanol, and ethylene glycol.

12. The method according to claim 10, wherein the diluent has solubility of 0 to 5 g in 100 g of water.

13. The method according to claim 12, wherein the water-soluble solvent comprises ethanol.

14. The method according to claim 1, wherein the diluent has solubility of 0 to 5 g in 100 g of water.

15. The method according to claim 1, wherein the water-soluble solvent comprises at least one of methanol, ethanol, n-propanol, isopropanol, n-butanol, tert-butanol, and ethylene glycol.

16. The method according to claim 7, wherein the concentrate includes fucoxanthin in an amount of 0.001 to 50% by weight.

17. The method according to claim 7, wherein the concentrate includes fucoxanthin in an amount of 0.01 to 50% by weight.

18. The method according to claim 1, further comprising:
   mixing the aggregate with a water-soluble solvent; and
   mixing a resultant mixture containing the aggregate with water and/or a water-soluble solvent such that a concentration of the water-soluble solvent is 20 to 45% by weight to produce an aggregate.

19. The method according to claim 18, wherein the water-soluble solvent mixed with the seaweed comprises ethanol.

20. The method according to claim 19, wherein the water-soluble solvent mixed with the aggregate comprises ethanol.

* * * * *